United States Patent
Marie-Rose et al.

(10) Patent No.: US 9,150,488 B2
(45) Date of Patent: Oct. 6, 2015

(54) PRODUCTION OF ACRYLIC ACID AND ETHANOL FROM CARBONACEOUS MATERIALS

(71) Applicants: Stephane Marie-Rose, Sherbrooke (CA); Esteban Chornet, Sherbrooke (CA)

(72) Inventors: Stephane Marie-Rose, Sherbrooke (CA); Esteban Chornet, Sherbrooke (CA)

(73) Assignee: Enerkem, Inc., Montreal, Quebec (CA)

( * ) Notice: Subject to any disclaimer, the term of this patent is extended or adjusted under 35 U.S.C. 154(b) by 0 days.

(21) Appl. No.: 13/894,567

(22) Filed: May 15, 2013

(65) Prior Publication Data

US 2014/0155650 A1 Jun. 5, 2014

Related U.S. Application Data

(60) Provisional application No. 61/663,112, filed on Jun. 22, 2012.

(51) Int. Cl.

| | |
|---|---|
| C07C 51/493 | (2006.01) |
| C07C 29/151 | (2006.01) |
| C07C 29/50 | (2006.01) |
| C07C 45/35 | (2006.01) |
| C07C 51/25 | (2006.01) |
| C01B 3/22 | (2006.01) |
| C07C 29/00 | (2006.01) |
| C07C 1/20 | (2006.01) |
| C10K 3/00 | (2006.01) |

(52) U.S. Cl.
CPC ................ *C07C 51/493* (2013.01); *C01B 3/22* (2013.01); *C07C 1/20* (2013.01); *C07C 29/00* (2013.01); *C07C 29/1518* (2013.01); *C07C 29/50* (2013.01); *C07C 45/35* (2013.01); *C07C 51/252* (2013.01); *C10K 3/006* (2013.01); *C01B 2203/0266* (2013.01); *C01B 2203/049* (2013.01); *C01B 2203/0485* (2013.01); *C01B 2203/061* (2013.01); *C10J 2300/0916* (2013.01); *C10J 2300/1665* (2013.01); *Y02E 50/18* (2013.01); *Y02E 50/32* (2013.01)

(58) Field of Classification Search
CPC ..................................................... C07C 51/493
See application file for complete search history.

(56) References Cited

U.S. PATENT DOCUMENTS

| | | | |
|---|---|---|---|
| 6,063,355 A | 5/2000 | Fujimura et al. | |
| 7,731,919 B2 | 6/2010 | Fukumoto | |
| 8,137,655 B2 | 3/2012 | Chornet et al. | |
| 8,192,647 B2 | 6/2012 | Chornet et al. | |
| 2007/0213567 A1 | 9/2007 | Ogawa et al. | |
| 2010/0099925 A1 | 4/2010 | Kharas | |
| 2010/0099926 A1 | 4/2010 | Kharas | |
| 2010/0224835 A1* | 9/2010 | Chornet et al. | 252/373 |
| 2012/0071688 A1* | 3/2012 | Herzog et al. | 562/599 |

FOREIGN PATENT DOCUMENTS

| | | |
|---|---|---|
| EP | 253409 | 1/1988 |
| EP | 293224 | 11/1988 |
| EP | 990636 | 4/2000 |
| WO | WO 2010/124077 | * 10/2010 |

* cited by examiner

*Primary Examiner* — Mark Shbuya
*Assistant Examiner* — Ana Z Muresan
(74) *Attorney, Agent, or Firm* — Raymond J. Lillie

(57) ABSTRACT

A process for producing acrylic acid from carbonaceous materials such as biomass. The carbonaceous material, such as biomass, is gasified to produce synthesis gas. The synthesis gas then is subjected to a plurality of reactions to produce acrylic acid.

13 Claims, 1 Drawing Sheet

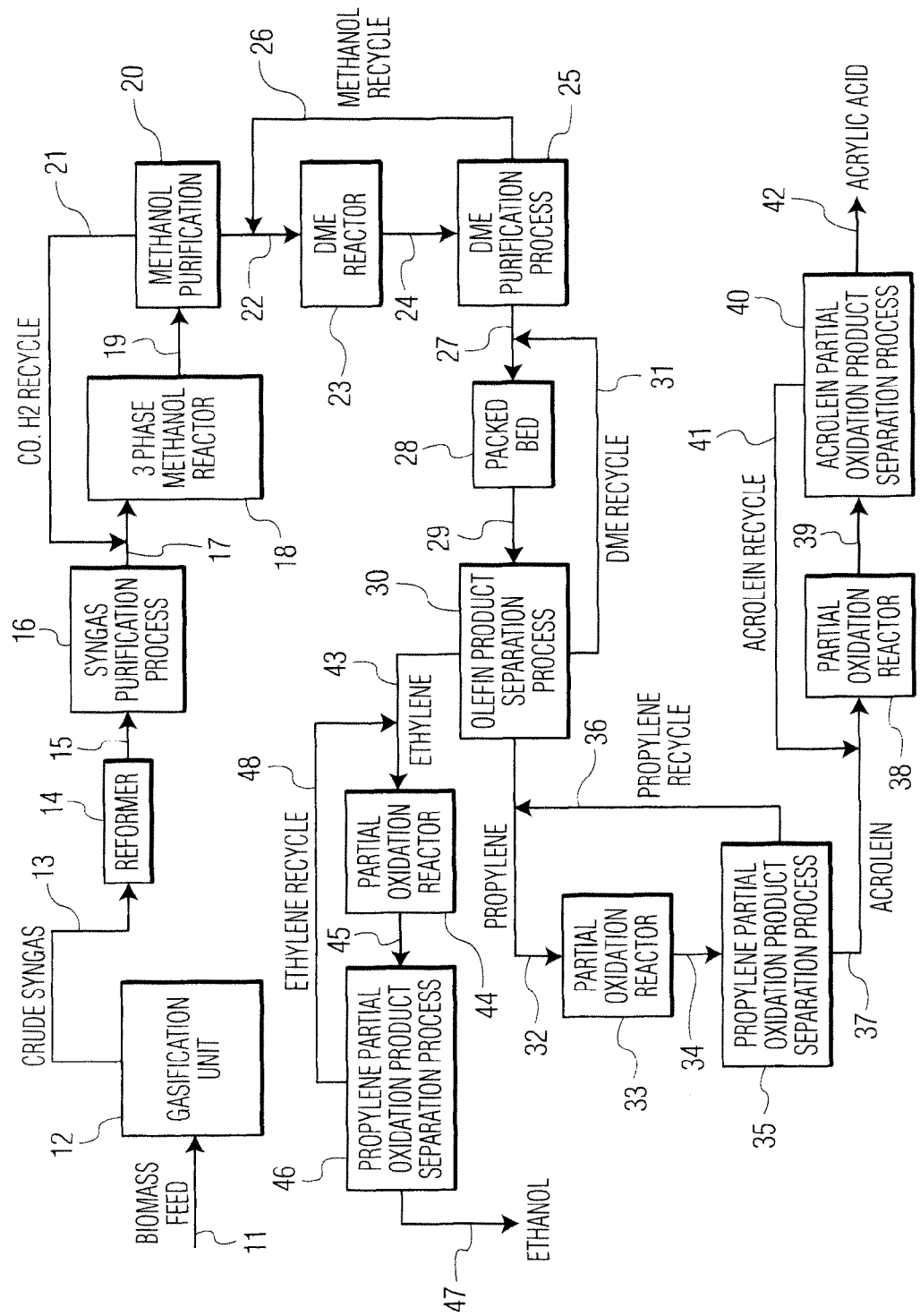

PRODUCTION OF ACRYLIC ACID AND ETHANOL FROM CARBONACEOUS MATERIALS

This application claims priority based on provisional Application Ser. No. 61/663,112, filed Jun. 22, 2012, the contents of which are incorporated by reference in their entirety.

This invention relates to the production of acrylic acid from carbonaceous materials, such as biomass, municipal solid wastes, and industrial waste materials. More particularly, this invention relates to gasifying carbonaceous materials to produce synthesis gas, and to producing acrylic acid and ethanol from such synthesis gas.

Synthesis gas, or syngas, includes carbon monoxide (CO) and hydrogen ($H_2$), with small amounts of carbon dioxide and residual hydrocarbons, and has a variety of uses. Synthesis gas may be used as a fuel gas in internal combustion engines, in gas turbines, as well as in gas fired steam boiler plants, or may be used to produce other desired materials, such as methanol and ethanol.

Synthesis gas may be produced by gasifying carbonaceous materials, such as residual biomass materials, such as forest residues agricultural residues, spent structural wood materials, and urban biomass, such as municipal solid waste, and industrial solid waste. The gasification of such materials provides a crude synthesis gas. The crude synthesis gas may be purified to remove impurities such as ammonia ($NH_3$), sulfur compounds (such as hydrogen sulfide ($H_2S$) and carbonyl sulfide (COS), chlorine compounds (such as HCl), volatile metals, tars, fines (in the form of sub-micron particles containing metals and metal salts), and char (solid particulates typically above 0.001 mm and containing carbon, metals, and metal salts). The purified syngas then may be used as a fuel or be used to produce other materials.

In accordance with an aspect of the present invention, there is provided a process for producing acrylic acid from a carbonaceous material. The process comprises gasifying the carbonaceous material to provide a crude synthesis gas. The crude synthesis gas then is purified to provide a purified synthesis gas. At least a portion of the carbon monoxide from the purified synthesis gas is reacted with hydrogen from the purified synthesis gas to produce methanol. The methanol then is reacted under conditions to provide a product comprising at least one olefin. The at least one olefin comprises propylene. The propylene is subjected to one or more reaction steps to produce acrylic acid.

In a non-limiting embodiment, the at least one olefin further comprises ethylene and the ethylene is reacted to produce ethanol.

In another non-limiting embodiment, the propylene is oxidized to produce acrylic acid.

In yet another non-limiting embodiment, the ethylene is oxidized partially to produce ethanol and the propylene is oxidized to produce acrylic acid.

Carbonaceous materials which may be gasified in accordance with the present invention include, but are not limited to, biomass-rich materials.

Biomass-rich materials which may be gasified in accordance with the present invention include, but are not limited to, homogenous biomass-rich materials, non-homogeneous biomass-rich materials, heterogeneous biomass-rich materials, and urban biomass.

In general, homogeneous biomass-rich materials are biomass-rich materials which come from a single source. Such materials include, but are not limited to, materials from coniferous trees or deciduous trees of a single species, agricultural materials from a plant of a single species, such as hay, corn, or wheat, for example, primary sludge from wood pulp, and wood chips.

Non-homogeneous biomass-rich materials in general are materials which are obtained from plants of more than one species. Such materials include, but are not limited to, forest residues from mixed species, and tree residues from mixed species obtained from debarking operations or sawmill operations.

Heterogeneous biomass-rich materials in general are materials that include biomass and non-biomass materials such as plastics, metals, and/or contaminants such as sulfur, halogens, or non-biomass nitrogen contained in compounds such as inorganic salts or organic compounds. Examples of such heterogeneous biomass-rich materials include, but are not limited to, urban biomass such as municipal solid waste, such as refuse derived fuel, solid recovered fuel, sewage sludge, used electrical transmission poles and railroad ties, which may be treated with creosote, pentachlorophenol, or copper chromium arsenate, and wood from construction and demolition operations which may contain one of the above chemicals as well as paints and resins.

In a non-limiting embodiment, prior to the gasification of the biomass, the biomass is admixed with at least one additive material, which neutralizes impurities such as chlorine, fluorine, and sulfur, which may be present in the biomass. In a non-limiting embodiment, the at least one additive is at least one adsorbent material. Such adsorbent materials include, but are not limited to, calcium oxide, or mixtures of calcium oxide, calcined limestone, ash materials, olivine (a silicate of iron and magnesium), and mixtures of calcium and magnesium oxides.

In another non-limiting embodiment, the at least one additive material is added to the biomass in an amount of from about 1.25 to about 3.0 times the stoichiometric quantity required for full neutralization of chlorine and other halogens, as well as sulfur present in the biomass. The term "neutralization," as used herein, includes the formation of stable salts such as $CaCl_2$, $CaF_2$, CaS, and the corresponding salts of magnesium and iron.

Gasification of the carbonaceous material, such as biomass, may be effected by means known to those skilled in the art. For example, in a non-limiting embodiment, the biomass may be gasified in a gasifier which includes a fluidized bed section and a reforming, or freeboard, section. Examples of such gasifiers are disclosed in published PCT Application Nos. WO2009/132449 and WO2010/069068.

In a non-limiting embodiment, the carbonaceous material, such as biomass, in a first step, is contacted in the fluidized bed section of the gasifier under conditions which effect a partial oxidation of the biomass. As a result of the partial oxidation, the biomass decomposes thermally, and there are produced a solid carbonaceous residue, gases, such as $CO_2$, steam, and some carbon monoxide and hydrogen, and vapors of intermediate species such as low molecular weight alkyl and aromatic hydrocarbons, and phenolics such as phenol, catechols, and methoxylated, alkylated, and alkoxylated phenols.

In a non-limiting embodiment, the biomass, in a first step, is heated in the fluidized bed section of a gasifier to a temperature of at least 500° C. and no greater than 1,000° C. In another non-limiting embodiment, the biomass, in the first step, is heated to a temperature of at least 550° C. and no greater than 900° C. In another non-limiting embodiment, the biomass, in the first step, is heated to a temperature of at least 550° C. and no greater than 800° C. In a further non-limiting embodiment, the biomass, in the first step, is heated to a temperature of at least 600° C. and no greater than 700° C. In yet another non-limiting embodiment, the biomass, in the first step, is heated to a temperature of at least 600° C. and no greater than 660° C.

In a non-limiting embodiment, the oxidizing gas, in the first step, further comprises nitrogen in an amount which does not exceed 80 vol.% of the oxidizing gas. In one non-limiting embodiment, the oxidizing gas includes oxygen-enriched air and steam, in which oxygen is present in an amount of up to about 40 vol.% of the oxidizing gas, and nitrogen is present in an amount that does not exceed 80 vol.% of the oxidizing gas.

In another non-limiting embodiment, the biomass, in the first step, is contacted with oxygen and steam in the absence of nitrogen. In a non-limiting embodiment, oxygen is present in such nitrogen-free gas in an amount about 5 vol. % to about 100 vol. %. In another non-limiting embodiment, oxygen is present in an amount of from about 5 vol. % to about 40 vol. %. In yet another non-limiting embodiment, oxygen is present in such nitrogen-free gas in an amount of from about 30 vol. % to about 40 vol. %.

In another non-limiting embodiment, the oxidizing gas, in the first step, includes carbon dioxide. In a further non-limiting embodiment, carbon dioxide is present in the oxidizing gas in an amount of from about 5 vol. % to about 100 vol. %. In a further non-limiting embodiment, carbon dioxide is present in the oxidizing gas in an amount of from about 5 vol. % to about 40 vol. %. In yet another non-limiting embodiment, carbon dioxide is present in the oxidizing gas in an amount of from about 10 vol. % to about 20 vol. %.

In a further non-limiting embodiment, oxygen is present in the oxidizing gas in an amount of from about 30 vol. % to about 40 vol. %, carbon dioxide is present in the oxidizing gas in an amount of from about 10 vol.% to about 20 vol. %, and the remainder of the oxidizing gas essentially is steam. Trace amounts of argon may be present.

In another non-limiting embodiment, the biomass, in the first step, is contacted with oxygen at a weight ratio of oxygen to biomass that biomass is from about 0.1 to about 0.5 times the stoichiometric weight ratio needed for complete combustion, i.e., total oxidation of the biomass.

In a further non-limiting embodiment, the biomass, in the first step, is contacted with oxygen at a weight ratio of oxygen to biomass of from about 0.2 to about 0.35 weight of the stoichiometric weight ratio needed for complete combustion of the biomass. In yet another non-limiting embodiment, the biomass is contacted with oxygen at a weight ratio of oxygen to biomass of from about 0.25 to about 0.30 of the stoichiometric weight ratio needed for complete combustion of the biomass.

In another non-limiting embodiment, in the first step, the biomass is contacted with oxygen and steam in a bed of particulate material, whereby the passage of oxygen and steam through such bed provides a fluidized bed of the particulate material. Such particulate materials include, but are not limited to, alumina, olivine, silica, anthracite, desulfurized petroleum coke, and in general, any stable refractory material. In a non-limiting embodiment, the particulate material is selected from the group consisting alumina, olivine and silica. In another non-limiting embodiment, the particles have a diameter of from about 50 microns to about 600 microns.

In another non-limiting embodiment, the biomass is contacted, in the first step, with oxygen and steam for a period of time that does not exceed 10 seconds. In a further non-limiting embodiment, the biomass is contacted, in the first step, with oxygen and steam for a period of time that does not exceed 3 seconds. In yet another non-limiting embodiment, the biomass is contacted, in the first step, with oxygen and steam for a period of time that does not exceed one second.

As the biomass is contacted with oxygen and steam in the first step, the biomass is oxidized partially, and is decomposed thermally, thereby producing a solid carbonaceous residue, gases such as $CO_2$, steam, and some carbon monoxide (CO) and hydrogen ($H_2$), and vapors of intermediate species such as low molecular weight alkyl and aromatic hydrocarbons, and phenolics as hereinabove described.

When the biomass is contacted with oxygen and steam, in the first step, in the presence of a fluidized bed, the solid carbonaceous residue produced in the first step remains in the fluidized bed and provides the bulk of the exothermal heat of oxidation, thereby maintaining the fluidized bed at the temperatures hereinabove described. The oxygen used in the first step essentially is consumed in such step, while a portion of the carbonaceous residue formed during the first step is consumed as well, and another portion of the carbonaceous residue is entrained as char. The char particles also may contain inorganic materials initially present in the biomass feedstock.

Some cracking of intermediates, i.e., low molecular weight hydrocarbons, phenolics, and aromatics, may occur during the first step; however, higher temperatures are required to convert the residual carbon in the entrained char particles, and additionally to crack and reform the intermediate vapors containing the low molecular weight alkyl and aromatic hydrocarbons, and phenolics. Thus, in a second step, at least a portion of the partially oxidized biomass produced in the first step is treated in the freeboard section of the gasifier with an oxidizing gas comprising oxygen and steam to heat the biomass to a temperature of at least 800° C. to produce synthesis gas.

In a non-limiting embodiment, the partially oxidized and thermally decomposed biomass, in the second step, is heated to a temperature of from about 800° C. to about 1,200° C. In another non-limiting embodiment, the oxidized biomass, in the second step, is heated to a temperature of from about 900° C. to about 1,100° C. In yet another non-limiting embodiment, the oxidized biomass, in the second step, is heated to a temperature of from about 925° C. to about 1,000° C.

In a non-limiting embodiment, the oxidizing gas, in the second step, further comprises nitrogen in an amount which does not exceed 60 vol. % of the oxidizing gas. In one non-limiting embodiment, the oxidizing gas includes oxygen-enriched air and steam, in which oxygen is present in an amount of up to about 40 vol. % of the oxidizing gas, and nitrogen is present in an amount that does not exceed 60 vol. % of the oxidizing gas.

In another non-limiting embodiment, the partially oxidized biomass, in the second step, is contacted with oxygen and steam in the absence of nitrogen. In a non-limiting embodiment, oxygen is present in such nitrogen-free gas in an amount which does not exceed 40 vol. %. In yet another non-limiting embodiment, oxygen is present in such nitrogen-free gas in an amount of from about 30 vol. % to about 40 vol. %.

In another non-limiting embodiment, the oxidizing gas, in the second step, further comprises carbon dioxide. In a further non-limiting embodiment, carbon dioxide is present in the oxidizing gas in an amount that does not exceed 20 vol.%. In yet another non-limiting embodiment, carbon dioxide is present in the oxidizing gas in an amount of from about 10 vol. % to about 20 vol. %.

In a further non-limiting embodiment, oxygen is present in such oxidizing gas in an amount of from about 30 vol. % to about 40 vol. %, carbon dioxide is present in the oxidizing gas in an amount of from about 10 vol. % to about 20 vol. %, and the remainder of the oxidizing gas essentially is steam. Trace amounts of argon may be present.

In a non-limiting embodiment, the oxidized biomass, in the second step, is treated with the oxygen and steam for a period of time of from about 0.5 seconds to about 10 seconds. In another non-limiting embodiment, the oxidized biomass, in the second step, is treated with the oxygen and steam for a period of time of from about 4 seconds to about 8 seconds.

Alternatively, in a further non-limiting embodiment, the oxidized biomass, in the second step, is treated with oxygen and steam in a first stage to a temperature of at least 800° C., followed by further treatment with oxygen and steam in a second stage. The oxidized biomass is heated to a temperature in the second stage which is higher than that of the first stage. In a non-limiting embodiment, the oxidized biomass is heated in the first stage to a temperature of at least 800° C. and does not exceed 850° C.

In another non-limiting embodiment, the oxidized biomass is heated in the second stage to a temperature of at least 900° C. In a further non-limiting embodiment, the oxidized biomass is heated in the second stage to a temperature of from about 900° C. to about 1,000° C. In yet another non-limiting embodiment, the oxidized biomass is heated in the second stage to a temperature of from about 925° C. to about 975° C.

In yet another non-limiting embodiment, the oxidized biomass is heated in the first stage to a temperature of from 800° C. to 850° C., and is heated in the second stage to a temperature of from 925° C. to 975° C.

When the oxidized biomass is contacted with oxygen and steam in the second step, whereby the oxidized biomass is heated to a temperature of at least 800° C., carbon in the char is converted fully by the steam to generate hydrogen and carbon monoxide, and steam reforming of the intermediates yields more hydrogen and carbon monoxide. In general, the inorganic materials which are present in the char in general are exposed to temperatures higher than their melting points. Such inorganic materials will melt and stay melted in the char particles. Deposition of char particles and/or inorganic materials on the walls of the gasification vessel is minimal because the particles are entrained under plug flow conditions.

In general, the gasifier is operated at a pressure that does not exceed 10 atm. The fluidized bed section includes particles of a fluidizable material, such as alumina or olivine, having a particle size of from about 50 microns to about 600 microns. Oxygen and steam are introduced into the fluidized bed section of the gasifier to provide a gas velocity of from about 0.7 m/sec. to about 1.5 m/sec., thereby providing a bubbling fluidized bed of the particulate material.

The gas and vapors produced in the fluidized bed section pass through the disengaging zone into the freeboard section, in which the gas and vapors are contacted with oxygen and steam to reach a temperature of from about 925° C. to about 1,000° C. The oxygen and steam are introduced into the freeboard section of the gasifier in such an amount that the velocity of the gaseous phase is maintained from about 0.3 m/sec. to about 0.7 m/sec. In general, gas residence times in the freeboard section of the gasifier are from about 4 seconds to about 8 seconds.

In the freeboard section, the phenolics are converted into simple aromatics, and tar cracking and tar reforming are effected. Carbon in the char essentially is converted fully by the steam and $CO_2$ to generate $H_2$ and CO, and steam reforming of the vapors of the intermediate hydrocarbons also generates $H_2$ and CO. Inorganic materials present in the char will melt. Deposition of inorganic materials on the walls of the gasifier, however, is minimal due to particle entrainment in the existing plug flow regime.

As noted hereinabove, in one alternative non-limiting embodiment, the heating of the partially oxidized biomass to produce synthesis gas may be effected in a combination of a first stage, and a second stage, wherein the partially oxidized biomass is heated to a temperature in the second stage which is greater than that of the first stage.

In one non-limiting embodiment, the first stage is conducted in the freeboard section of the gasifier, and the second stage is conducted in one or more tubular flow reactors. In a non-limiting embodiment, the one or more tubular flow reactor(s) is (are) in the form of refractorized and insulated carbon steel pipes. In another non-limiting embodiment, the heating in the second stage is conducted in two tubular flow reactors which are connected to each other so as to form a U-shaped configuration.

In a non-limiting embodiment, the oxidized biomass is contacted with oxygen and steam in the freeboard section of the gasifier at a temperature of from about 800° C. to about 850° C. The oxygen and steam are introduced into the freeboard section of the gasifier in such amounts that maintain a gaseous velocity of from about 0.3 m/sec. to about 0.7 m/sec., and the reaction time is from about 4 seconds to about 8 seconds, as hereinabove described, to begin the conversion of the oxidized biomass to a crude synthesis gas. The gas produced in the freeboard section also has char particles entrained therein.

The gas and entrained particles then are passed from the freeboard section of the gasifier to one or more tubular flow reactors. In a non-limiting embodiment, additional oxygen and steam are added to the tubular flow reactor(s). In the tubular flow reactor(s), the gas is heated to a temperature of from about 925° C. to about 975° C., and in general, the reaction time in the tubular flow reactor(s) is from about 1 second to about 2 seconds, which is sufficient to complete the conversion of the oxidized biomass to a crude synthesis gas.

A crude synthesis gas product thus is produced by gasifying biomass in the fluidized bed and freeboard sections of the gasifier, and optionally in one or more tubular flow reactors, under the conditions hereinabove described. Such crude synthesis gas then is conditioned to provide a clean synthesis gas.

In a non-limiting embodiment, crude synthesis gas is cooled, and then passed through one or more cyclones to remove larger particles, such as char particles. In a non-limiting embodiment, the particles removed by the one or more cyclones have a size over 10 microns.

After the particles have been removed from the crude synthesis gas, the crude synthesis gas may be scrubbed in a scrubbing system to remove fines and impurities such as HCl, $H_2S$, and ammonia, as well as sodium salts and tar, to provide a purified synthesis gas. Examples of the preparation of a crude synthesis gas, and of the purification of a crude synthesis gas are described in published PCT Application Nos. WO2010/069068 and WO2009/132449, the contents of which are incorporated by reference.

Once a purified synthesis gas is produced, at least a portion of the hydrogen and at least a portion of the carbon monoxide in the synthesis gas are reacted to produce methanol. In a non-limiting embodiment, a portion of the hydrogen and a portion of the carbon monoxide in the synthesis gas are reacted in the presence of a suitable methanol synthesis catalyst, such as a copper oxide based catalyst, such as a Cu/ZnO/$Al_2O_3$ catalyst or a Cu/ZnO catalyst in oil, to produce methanol. In a non-limiting embodiment, the catalyst may be on stream for at least 5,000 hours before regeneration. In another non-limiting embodiment, the hydrogen and carbon monoxide are reacted to produce methanol at a ratio of hydrogen to carbon monoxide of from about 0.6:1 to about 3:1.

In general, the hydrogen and carbon monoxide are reacted to produce methanol according to the following equation:

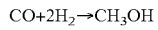

$$CO + 2H_2 \rightarrow CH_3OH$$

In a non-limiting embodiment, the methanol then is subjected to dehydration to produce at least one ether, such as dimethyl ether, or DME, according to the following equation:

$$2CH_3OH \rightarrow CH_3OCH_3 + H_2O$$

The methanol may be subjected to dehydration to produce dimethyl ether in the presence of a dehydration catalyst. In a non-limiting embodiment, the dehydration catalyst is gamma-alumina.

In a non-limiting embodiment, the hydrogen and carbon monoxide of the synthesis gas are reacted at a pressure of from about 250 to about 2,000 psi. In another non-limiting embodiment, the hydrogen and carbon monoxide are reacted at a pressure of from about 300 to about 1,500 psi. In another non-limiting embodiment, the hydrogen and carbon monoxide are reacted at a temperature of from about 100° C. to about 300° C. In another non-limiting embodiment, the hydrogen and carbon monoxide are reacted at a molar ratio of from about 1:1 to about 3:1.

In a further non-limiting embodiment, the hydrogen and carbon monoxide are reacted in the presence of an "integrated" methanol synthesis and dehydration catalyst which may be suspended in an inert oil, such as white mineral oil or Drakeol, into which the hydrogen and carbon monoxide are bubbled. In such an embodiment, the hydrogen and carbon monoxide are reacted in the presence of the "integrated" catalyst to produce methanol. The methanol then is reacted immediately in the presence of the "integrated" catalyst to produce dimethyl ether and water.

In a non-limiting embodiment the hydrogen and the carbon monoxide are reacted in the presence of a methanol catalyst in a first reactor to produce methanol, and then the methanol is reacted in the presence of a dehydration catalyst in a second reactor to produce at least one ether, such as DME.

The DME then is purified to remove the residual hydrogen, carbon monoxide and water. The purified DME then is passed to a reactor such as, for example, in a non-limiting embodiment, a packed bed reactor to produce a product that comprises at least one olefin, wherein the at least one olefin includes propylene. The synthesis of the at least one olefin, including propylene, in a non-limiting embodiment, is carried out in a fixed bed reactor using an acid catalyst at 200 to 550° C. and 1 to 30 atm. Catalysts which may be used for this reaction include, but are not limited to, one or more zeolites, gamma alumina, or other acidic materials.

The DME is reacted to produce olefins, methane, and aromatics. Olefins which may be produced by reacting DME as hereinabove described include propylene and ethylene. Depending upon the catalyst used for the olefin synthesis, the propylene selectivity may be between 70% and 95%.

In a non-limiting embodiment, the propylene is oxidized to acrolein. This reaction, in a non-limiting embodiment, is carried out in a fixed bed reactor in the temperature range 250 to 450° C. Catalysts used for this reaction may be, but are not limited to, multicomponent metal oxide based catalysts. In a non-limiting embodiment, the catalyst is an Mo—Bi based catalyst. Examples of such catalysts are described in Nojiri, et al., *Science and Engineering*, Vol. 37, pgs. 145-170 (1995), U.S. Pat. No. 7,731,919, and published U.S. Patent Application No. 2007/0213567.

The acrolein then is reacted in another oxidation reactor to produce acrylic acid. After the acrolein is reacted in the oxidation reactor to produce acrylic acid, any unreacted acrolein is separated for the acrylic acid and is recycled to the acrolein oxidation reactor, and the resulting acrylic acid product is recovered.

Alternatively, in a non-limiting embodiment, the propylene is reacted in a partial oxidation reactor to produce acrylic acid in the presence of a cobalt and nickel molybdate based catalyst.

BRIEF DESCRIPTION OF THE DRAWING

The invention now will be described with respect to the drawing, wherein

The drawing is a schematic of an embodiment of a process for producing acrylic acid in accordance with a non-limiting embodiment of the present invention.

Referring now to the drawing, a biomass feed in line 11 is fed to gasification unit 12 to provide a crude synthesis gas. The crude synthesis gas is withdrawn from gasification unit through line 13 and is subjected to thermal reforming in reformer 14 to provide additional synthesis gas. The resulting crude synthesis gas is withdrawn from reformer 14 through line 15 and is subjected to a series of purification steps, indicated schematically as 16. The purified synthesis gas then is passed to line 17 and into three phase methanol reactor 18, which contains a catalyst suspended in an inert oil.

In the methanol reactor 18 the carbon monoxide and hydrogen of the purified synthesis gas are reacted to produce methanol. The methanol containing product is withdrawn from reactor 18 through line 19 and is subjected to a purification process, indicated schematically as 20. The carbon monoxide and the hydrogen are separated from the methanol and are recycled through line 21 to line 17. Purified methanol is passed through line 22 to packed bed reactor 23 wherein the methanol is reacted to form an ether product, mainly dimethyl ether. The dimethyl ether containing product is withdrawn from the reactor 23 through line 24 and is subjected to a purification process, indicated schematically as 25. Unreacted methanol is separated from the DME and water and is recycled through line 26 to line 22. Water generated from the DME synthesis could be used for heat generation.

Purified DME is passed though line 27 to a packed bed reactor 28 wherein the DME is reacted to form an olefin product including ethylene and propylene. The olefin product is withdrawn form the reactor 28 through line 29 and is subjected to a separation process, indicated schematically as 30.

Unreacted DME is separated from the ethylene and propylene and recycled through line 31 to line 27.

Propylene is withdrawn form separation process 30 through line 32 and is passed to partial oxidation reactor 33 where propylene is reacted to produce acrolein. The acrolein and the unreacted propylene are withdrawn from the partial oxidation reactor 33 through line 34 and then are subjected to a separation process, indicated schematically as 35. Unreacted propylene is withdrawn form the separation process 35 through line 36 and is recycled to line 32. Acrolein is withdrawn from separation process 35 through line 37 and is passed to partial oxidation reactor 38 where the acrolein is reacted to produce acrylic acid. Acrylic acid and unreacted acrolein are withdrawn from the partial oxidation reactor 38 through line 39 and then are subjected to a separation process indicated schematically as 40. Unreacted acrolein is withdrawn from separation process 40 through line 41 and is recycled to line 37. Acrylic acid is recovered from separation process 40 through line 42.

Ethylene is withdrawn from the separation process 30 through line 43 and passed to partial oxidation reactor 44, where ethylene is reacted with oxygen to produce ethanol. Ethanol and unreacted ethylene are withdrawn from the partial oxidation reactor 44 through line 45 and are subjected to a separation process, indicated schematically at 46. Unreacted ethylene is withdrawn from separation process 46 through line 48 and recycled to line 43. Ethanol is recovered form separation process 46 through line 47.

The disclosures of all patents and publications, including published patent applications, are incorporated herein by reference as if each patent and publication were incorporated individually by reference.

It is to be understood, however, that the scope of the present invention is not to be limited to the specific embodiments described above. The invention may be practiced other than as particularly described and still be within the scope of the accompanying claims.

What is claimed is:

1. A process for producing acrylic acid and ethanol from biomass comprising:
    (a) contacting said biomass with an oxidizing gas comprising oxygen and steam at a temperature of at least 550° C. and no greater than 800° C., thereby oxidizing said biomass;
    (b) treating at least a portion of said oxidized biomass produced in step (a) with an oxidizing gas comprising oxygen and steam to heat said oxidized biomass to a temperature which is at least 800° C. and does not exceed a maximum of 850° C.;
    (c) treating at least a portion of said oxidized biomass produced in step (b) with an oxidizing gas comprising oxygen and steam to heat said oxidized biomass to a temperature which is at least 900° C. and does not exceed a maximum of 1000° C., thereby producing a crude synthesis gas;
    (d) purifying the crude synthesis gas to provide a purified synthesis gas;
    (e) reacting at least a portion of the carbon monoxide from said purified synthesis gas with hydrogen from said purified synthesis gas to provide methanol;
    (f) reacting said methanol in the presence of a dehydration catalyst to produce dimethyl ether;
    (q) reacting said dimethyl ether to provide a product comprising propylene and ethylene;
    (h) reacting said ethylene to produce ethanol; and
    (i) subjecting said propylene to one or more reaction steps to produce acrylic acid.

2. The process of claim 1 wherein, in step (c), said biomass is heated to a temperature of from about 925° C. and no greater than 975° C.

3. The process of claim 1 wherein, in step (e), said carbon monoxide and said hydrogen are reacted in the presence of a methanol synthesis catalyst.

4. The process of claim 1 wherein said dimethyl ether is reacted in the presence of an acid catalyst.

5. The process of claim 4 wherein said acid catalyst is selected from the group consisting of zeolites and gamma alumina.

6. The process of claim 1 wherein, in step (i), said propylene is reacted in a partial oxidation reactor to produce acrylic acid in the presence of a cobalt and nickel molybdate based catalyst.

7. The process of claim 1 wherein, in step (i), said propylene is oxidized to produce acrolein, and said acrolein is reacted in an oxidation reactor to produce acrylic acid.

8. The process of claim 1 wherein, prior to step (a), said biomass is admixed with at least one additive material which neutralizes impurities which may be present in said biomass.

9. The process of claim 8 wherein said impurities are selected from the group consisting of chlorine, fluorine, and sulfur.

10. The process of claim 8 wherein said at least one additive material is at least one adsorbent material.

11. The process of claim 10 wherein said at least one adsorbent material is selected from the group consisting of calcium oxide, calcined limestone, ash materials, olivine, and mixtures of calcium and magnesium oxides.

12. The process of claim 1 wherein steps (a) and (b) are conducted in a gasifier, said gasifier having a fluidized bed section and a freeboard section, and wherein step (a) is conducted in said fluidized bed section and step (b) is conducted in said freeboard section.

13. The process of claim 12 wherein step (c) is conducted in one or more tubular flow reactors.

\* \* \* \* \*